United States Patent [19]
Gentelia et al.

[11] Patent Number: 5,766,165
[45] Date of Patent: Jun. 16, 1998

[54] RETURN PATH MONITORING SYSTEM

[76] Inventors: John S. Gentelia, 3264 Center Rd., Madison, N.Y. 13402; Ernesto G. Sevilla, 927 Ridgewood Rd., Herkimer, N.Y. 13350

[21] Appl. No.: 532,143

[22] Filed: Sep. 22, 1995

[51] Int. Cl.$^6$ .................................................. A61B 17/39
[52] U.S. Cl. .................................. 606/35; 606/34; 606/42
[58] Field of Search .......................... 606/32–35, 37–42, 606/45–50

[56] References Cited

U.S. PATENT DOCUMENTS

| | | |
|---|---|---|
| 1,620,828 | 3/1927 | Molony . |
| 1,620,929 | 3/1927 | Wallerich . |
| 1,713,971 | 5/1929 | Lowry et al. . |
| 1,770,653 | 7/1930 | Molony . |
| 1,919,543 | 7/1933 | Doane . |
| 4,085,756 | 4/1978 | Weaver . |
| 4,116,198 | 9/1978 | Roos . |
| 4,184,492 | 1/1980 | Meinke et al. . |
| 4,244,371 | 1/1981 | Farin ........................................ 606/34 |
| 4,706,667 | 11/1987 | Roos . |
| 4,907,589 | 3/1990 | Cosman . |

*Primary Examiner*—Michael Peffley
*Attorney, Agent, or Firm*—Larson & Taylor

[57] ABSTRACT

A controlled return path monitoring system is used in combination with an electrosurgical generator unit employing an active electrode for performing electrosurgery. The system includes internal electrode which is disposed, in use, within the body of a patient in proximity to the active electrode and is electrically connected to the electrosurgical generator unit so as to provide a preferred current return path back to the electrosurgical generator unit, and an external electrode which is disposed, in use, on the body of the patient and is electrically connected to the electrosurgical generator unit so as to provide a safety current return path back to the electrosurgical generator unit. A detector monitors the return current flow from the two electrodes back to the electrosurgical generator unit and controls the unit in accordance with the monitored return current flow, e.g., shuts off the unit when the flow exceeds a predetermined level.

3 Claims, 1 Drawing Sheet

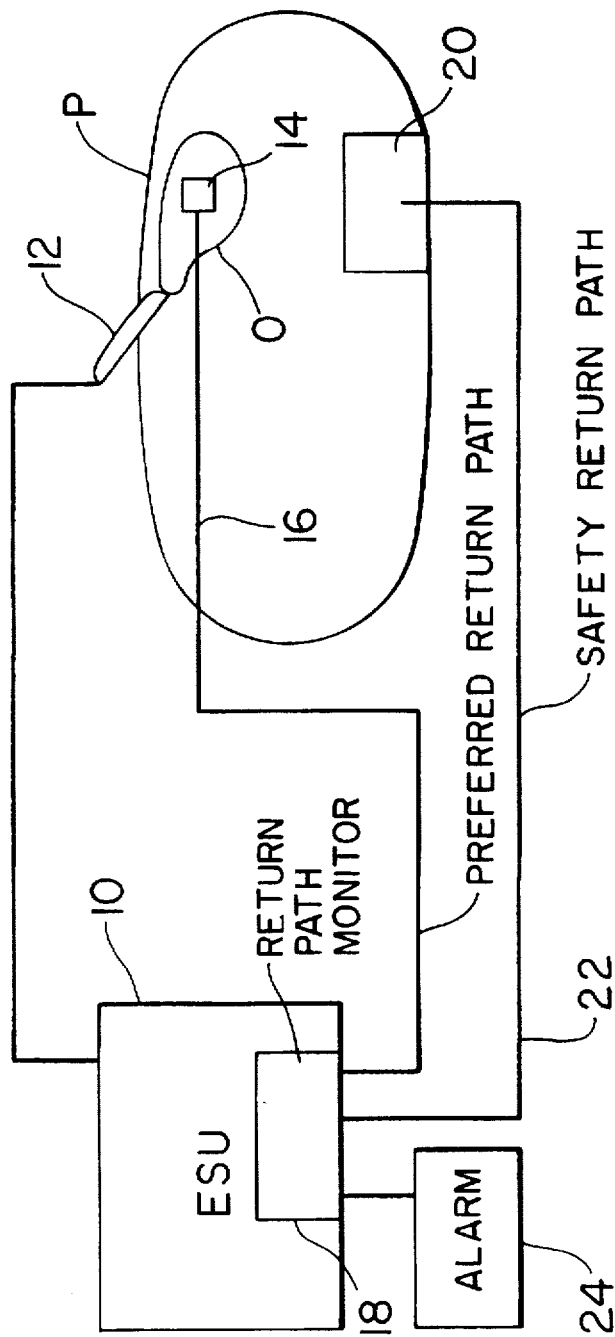

RETURN PATH MONITORING SYSTEM

FIELD OF THE INVENTION

The present invention relates to return path monitors for monitoring the return current from the active electrode of an electrosurgical generator.

BACKGROUND OF THE INVENTION

Advocates of various competing modalities in area of minimally invasive surgical procedures such as procedures using lasers, ultrasound, conventional surgery and even bipolar electrosurgery having been critical of monopolar electrosurgery and have argued that monopolar electrosurgery is unsafe for certain procedures in view of the unexplained tissue damage that has occurred in some instances in the past. Much of this concern focuses on the return path of the electrosurgical current and the difficulty of predicting the actual path taken by the monopolar electrosurgical energy. Some of the factors that influence the return path, and thus contribute to the unexplained tissue damage, are of greater importance in minimally invasive surgical procedures but these factors can also be critical in other procedures.

In most conventional electrosurgical systems, a return electrode, usually in the form of a pad or plate, is applied externally, and is designed to return comparatively large currents from procedures such as TURS and the like. Using this type of grounding system for minimally invasive procedures makes it more difficult to predict the electrosurgical current return path.

Thus, a general problem with electrosurgical generators employing a monopolar active electrode is the uncertainty as to which path the return current is taking. For example, the current path could be through the bowels and arcing through the bowels could cause an internal burn. Another example of a problem in this area concerns the appendix. In operating, it is common practice to cut off the blood supply to the appendix and then cauterize. If more cutting is then to be done, the appendix will then act as an insulator (because of the cut off of blood flow thereto) and thus arcing through the bowels could again occur.

The prior art includes a number of specialized grounding electrodes. U.S. Pat. No. 4,085,756 (Weaver) discloses an apparatus for performing electrosurgical procedures such cutting and coagulating the fallopian tubes of the human female including ground terminal or electrode that is inserted into the uterine cavity so as to be positioned very close to the active electrode and thus provide a ground return path. Because of the close spacing of the active electrode and the ground terminal the current travels a very short distance within the body to the ground terminal and this is stated in the patent to reduce the possibility of burns or other injury associated with the use of conventional external ground plates, i.e., ground plates or electrodes that contact the exterior surface of the body of a patient. Other patents of interest include U.S. Pat. Nos. 1,620,925 (Wallerich), 1,620,828 (Malony), 1,770,653 (Molony), 1,713,971 (Lowry et al.), 1,919,543 (Doane), 4,184,492 (Meinke et al.), all of which disclose plates or electrodes placed near the active electrode, and U.S. Pat. No. 4,907,589 (Cosman) which includes a reference or ground electrode arrangement of interest. U.S. Pat. Nos. 4,706,667 (Roos) and 4,116,198 (Roos) disclose specialized active and neutral electrode assemblies.

SUMMARY OF THE INVENTION

In accordance with the invention, there is provided a current return path monitor system for an electrosurgical generator employing a monopolar active electrode which overcomes or greatly reduces the problems discussed above with respect to "phantom burns" and like phenomena, thereby increasing the effectiveness of monopolar electrosurgery. The invention also increases the safety of bipolar electrosurgery by providing one or more safety return paths in addition to the return path afforded by the bipolar electrode. Other advantages include reduced insulation needs due to lower voltage requirements, the capability of providing monitored return connectors for uninsulated non-electrosurgical instruments, the elimination of alternate burn sizes, and the ease of use wherein all electrosurgical instruments are plugged in and set up at the beginning of the procedure, thereby eliminating fumbling for cords, connectors, adapters and the like.

In accordance with a preferred embodiment of the invention, a controlled return path monitoring system is provided for use in combination with an electrosurgical generator unit, the system comprising: a first, internal electrode disposed, in use, within the body of a patient in proximity to the active electrode and electrically connected to the electrosurgical generator unit so as to provide a preferred current return path back to the electrosurgical generator unit; a second, external electrode disposed, in use, on the body of the patient and connected to the electrosurgical generator unit so as to provide a safety current return path back to the electrosurgical generator unit; and monitoring means for monitoring the return current flow from the first and second electrodes back to the electrosurgical generator unit and for controlling that unit in accordance with the monitored return current flow.

In one embodiment, the monitoring means comprises means for monitoring the current levels in the preferred return path and the safety return path. Advantageously, the monitoring means comprises means for comparing the current levels in the preferred return path and the safety return path, and for shutting off the electrosurgical generator unit when a predetermined relative change between the two levels is detected.

Other features and advantages of the invention will be set forth in, or apparent from, the following detailed description of preferred embodiments of the invention.

BRIEF DESCRIPTION OF THE DRAWINGS

FIG. 1 is a schematic diagram of an electrosurgical generator unit incorporating the current return path monitoring system of the invention and being used in a surgical procedure.

DESCRIPTION OF THE PREFERRED EMBODIMENTS

Referring to FIG. 1, a schematic diagram is provided of a preferred embodiment of the return path monitoring system of the invention is shown. The system includes an electrosurgical generator unit or ESU 10 employing a monopolar active electrode 12 which provides the requisite electrosurgical action such as cutting, coagulation or "blended" cutting and coagulation. FIG. 1 schematically illustrates the use of active electrode 12 in the removal of an organ O of a patient P.

A first, internal electrode 14 is provided within the patient near the operating site, i.e., the site of the active electrode 12 and is connected by a cable or other conductor 16 to a return path monitor 18 which, in the illustrated embodiment, forms part of generator 10. The connection between internal electrode 14 and monitor 18 is the preferred return path for electrosurgical current.

A second, external electrode 20 is connected to patient externally of the body and can be formed by a conventional ground pad or plate. External electrode 20 is connected by a cable or the like, denoted 22, to monitor 18 and electrode 20, together with cable 22, provides a safety return path.

Because of the close proximity of the internal electrode 14 to the operating site, there is normally very little current flow from the external electrode 20 through cable 22, i.e., most of the current will flow through the organ O (e.g., the appendix of the patient P) to internal electrode 14 and back to monitor 18 through return path or cable 16. However, if the organ O becomes an insulator because the blood supply thereto is cut off as in the situation discussed above, a change in current flow, e.g., an increase in flow in return path 22 and a decrease in current flow in return path 16, will be detected by monitor 18 which then initiates a control action such as cutting off the generator 10, activating an alarm indicated at 24, or both.

It is to be understood that internal electrode 14 can take a number of different forms including that of (i) metal graspers or the like which would be used to hold or grip a portion of the organ O to be removed, (ii) an internal electrode of a shape permitting it to be inserted into the body at the area of the operating site, and (iii) a metal grounding sheath on the outer surface of an endoscope or like instrument and insulated from the cutting element. The graspers can be of a conventional type (except for being connected to the return port of the ESU 10) or can be a specialized construction including wider jaws to increase contact area or conductive suction cups or the like to enhance gripping. The internal electrode referred to above can comprise a suction cup or pad, a small adhesive backed contact pad, an attachable clip or the like, with the electrode being placed on the desired area through a cannula. In accordance with another important embodiment, a pool or bath of saline or another conductive liquid located near the operating site can be used on the electrode. Of course, saline is often applied to this site in conventional surgical procedures and this saline itself can be used or can be augmented as necessary.

It will be appreciated that the power levels required for laparoscopic surgery are relatively low (on the order of 30 watts) and the impedance is low because of the blood at the site so that a much smaller electrode is required. Moreover, as noted above, an electrode, as such, can be dispensed with by using the saline bath as the electrode and providing an electrical connection to the bath. It will also be understood that the greatest temperature rise will occur at an electrode providing the smallest contact area but that this is not a problem where the electrode is attached to the organ to be removed because the organ is going to be thrown away in any event.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A controlled return path monitoring system in combination with an electrosurgical generator unit including an active electrode for performing electrosurgery, said system comprising:

a first, internal electrode disposed, in use, within the body of a patient in proximity to the active electrode and electrically connected to the electrosurgical generator unit so as to provide a preferred current return path providing a substantial current flow back to the electrosurgical generator unit under normal operating conditions;

a second, external electrode disposed, in use, on the body of the patient and electrically connected to the electrosurgical generator unit so as to provide a safety current return path providing a further current flow, back to the electrosurgical generator unit, which, under said normal operating conditions, is less than the current flow in said preferred current flow path; and monitoring means for monitoring the return current flow from said first and second electrodes back to the electrosurgical generator unit and for controlling the unit in accordance with the monitored return current flow.

2. A system as claimed in claim 1 wherein said monitoring means comprises means for monitoring the current levels in the preferred return path and the safety return path.

3. A system as claimed in claim 1 wherein said monitoring means comprises means for comparing the current levels in the preferred return path and the safety return path, and for shutting off the electrosurgical generator unit when a predetermined relative change between said levels is detected.

* * * * *